United States Patent [19]
Brown et al.

[11] Patent Number: 5,157,463
[45] Date of Patent: Oct. 20, 1992

[54] METHOD FOR DETERMINING SOLDER QUALITY

[75] Inventors: Mark D. Brown, Carrollton; Stephen B. Kaiser, Flower Mound; Lavaughn J. Dawson, Allen, all of Tex.

[73] Assignee: Texas Instruments Incorporated, Dallas, Tex.

[21] Appl. No.: 657,231

[22] Filed: Feb. 15, 1991

[51] Int. Cl.$^5$ .................... G01B 11/00; H04N 7/18
[52] U.S. Cl. ................................ 356/394; 356/237; 358/106
[58] Field of Search .............. 356/394, 398, 237; 382/8; 358/101, 106, 107

[56] References Cited

U.S. PATENT DOCUMENTS 4,242,702 12/1980 Kuni et al. .................... 356/394
4,695,157 9/1987 Schoenbaum et al. .......... 356/237

*Primary Examiner*—Richard A. Rosenberger
*Assistant Examiner*—Hoa Pham
*Attorney, Agent, or Firm*—B. Peter Barndt; Richard L. Donaldson

[57] ABSTRACT

A method for detecting defects in solder coatings on leads for electronic components maps the surface of the lead, detects light from the coated lead, and distinguishes defects in the coating based on the amount of reflected light.

11 Claims, 3 Drawing Sheets

METHOD FOR DETERMINING SOLDER QUALITY

FIELD OF THE INVENTION

This invention relates to a system and inspection method, and more particularly to a system and method for inspecting the quality of a solder coating on surfaces such as leads on electronic components.

BACKGROUND OF THE INVENTION

Component solderability is an industry wide problem which, if not detected, can result in excessive board joint rework and system failures. In the Defense Industry, the majority of military contracts require that samples from component lots be inspected for solderability per MIL-STD-202, Method 208. This inspection task is highly labor intensive and susceptible to human error.

Typically, samples of the components to be tested are selected and tested under military specified conditions to gauge the solder wetting ability on the component leads. MIL-STD-202, Method 208 specifies the operational requirements for all the equipment to be used in the test and the evaluation criteria to determine if the solder dipped components pass or fail. The critical area of the evaluation process is the visual examination of the solder coverage on the leads after the solder dip operation. The requirements specify that a specially trained and certified inspector perform a "visual" measurement of the solder coating at 10 power magnification with a "shadowless" light source. The 1-inch portion of the dipped lead nearest the component, or the whole lead if it is less than 1 inch long, is examined. If the new solder coating doesn't cover at least 95% of the lead then the specimen has failed the test. Visual determination of the solder coverage makes it very hard to get accurate and repeatable results. Even though a limited number of components are selected from each lot, the inspection operation through a microscope is very tedious. The only "tool" that has been available to help in this measurement is a grid reticle that fits in the eyepiece of a microscope. This requires the inspector to count the squares that the defects occupy and gauge against the 95% coverage criteria. Unfortunately, the grid is not very effective at the required 10x magnification.

The examination of each component requires inspectors to visually measure the total solder coverage. Components failing to meet a minimum of 95% solder coverage or components with large defect regions are rejected. When the length or diameter of the leads changes, it is even more difficult for the inspector to gauge the percent coverage. Another problem in the inspection process is the inspection lighting. A number of lighting techniques commonly used, such as ring lights and multi-point light sources, make it very difficult to identify surface defects on the lead.

BRIEF SUMMARY OF THE INVENTION

The invention is a system and method of inspecting the solder coating on a component lead to determine if the lead has at least a 95% coverage of solder. The component is inserted into an illuminated viewing chamber and inspected with a vision system. If the lead is a wire, the wire is rotated in segments to view the entire surface in several steps. Each viewed segment is inspected for solder coverage, and the percentage of coverage is determined. The coverage of each surface is averaged with the coverage of the other inspected segments to determine the total solder coverage of the lead. Other steps in the process include light chamber calibration, statistical output of the data for the scanned component, visual display of inspected area, and establishment of a reference on the component prior to inspection.

The technical advance represented by the invention as well as the objects thereof will become apparent from the following detailed description of a preferred embodiment of the invention when considered in conjunction with the accompanying drawings, and the novel features set forth in the appended claims.

DESCRIPTION OF A PREFERRED EMBODIMENT

Figure 1:
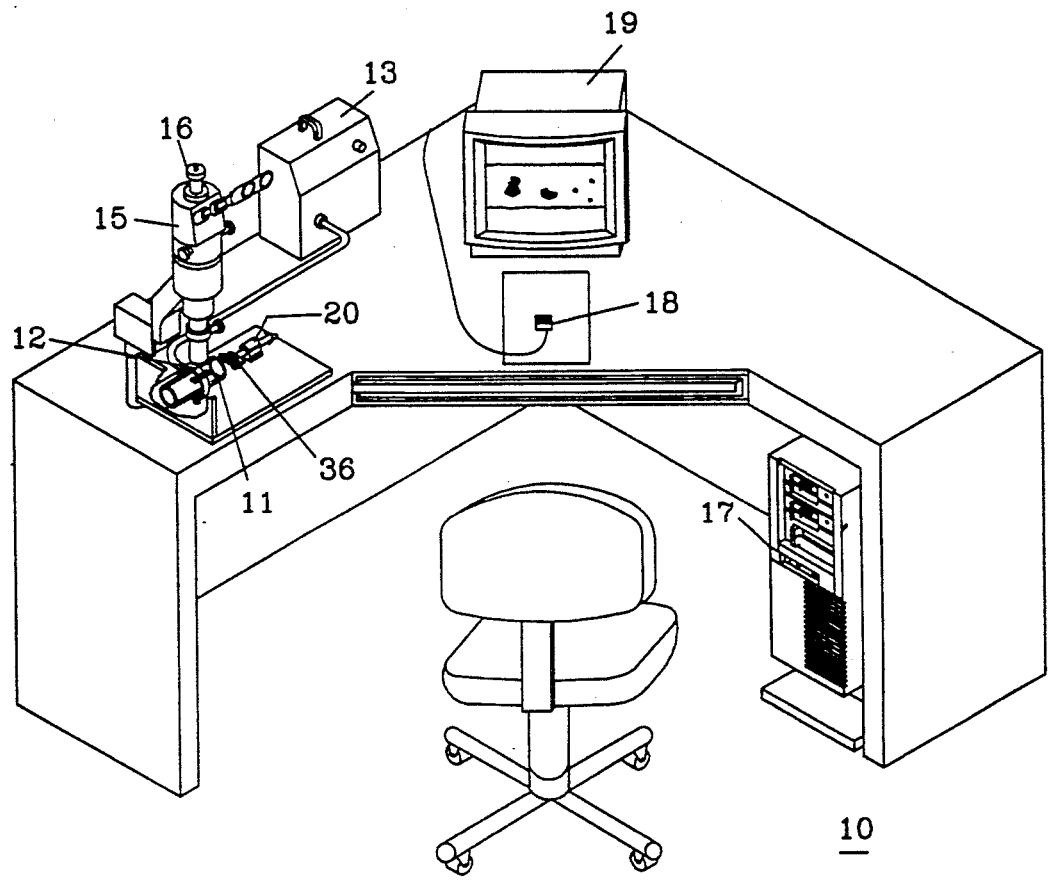
FIG. 1 illustrates the system used in practicing the method of the invention.
Figure 2:
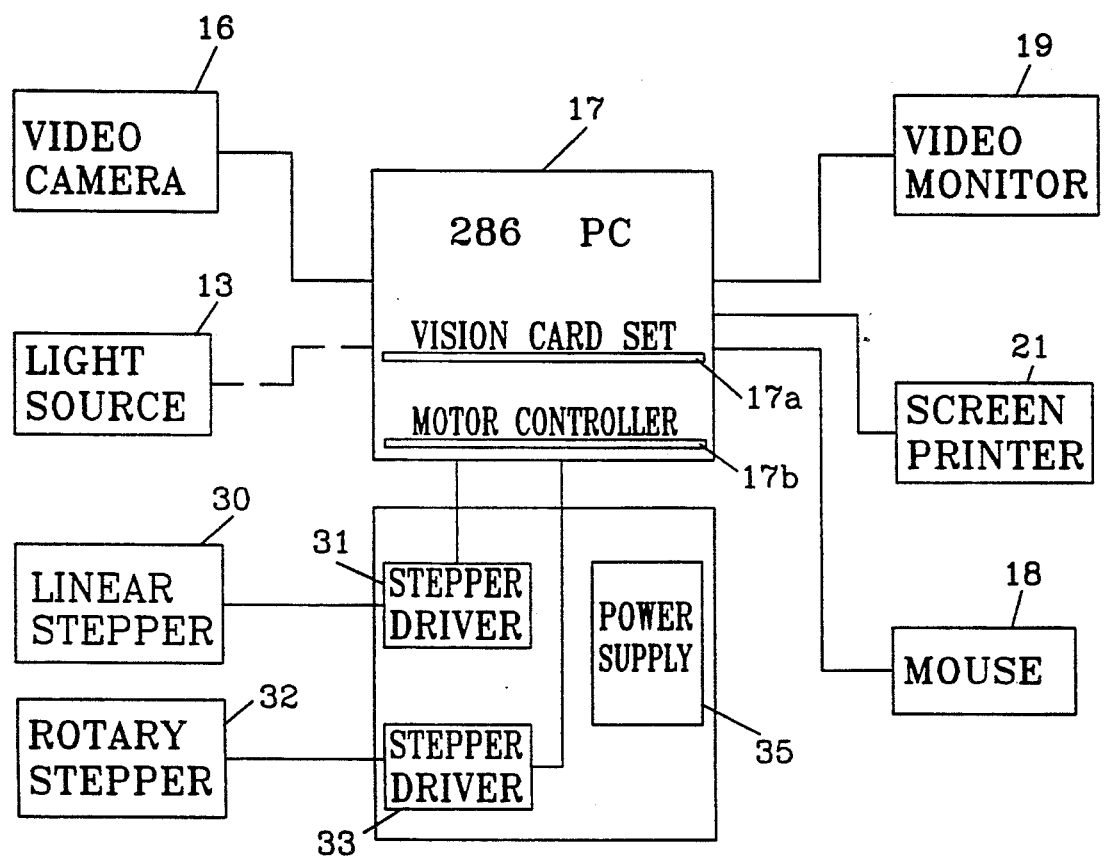
FIG. 2 is a block diagram of the system and controls of the system of FIG. 1.

The system, that utilizes the method of the present invention, illustrated in FIGS. 1 and 2, utilizes a custom designed chamber 11 which produces even, diffused lighting on all surfaces of the component being inspected. The light chamber, described and claimed in U.S. Pat. application Ser. No. 495,826, Filed Mar. 19, 1990, entitled APPARATUS AND METHOD FOR INSPECTION, is cylindrical in shape, and machined out of a translucent plastic. The plastic was selected to provide a consistent light diffusing characteristic and easy machining properties. An inspection port is machined into the chamber to allow the illuminated lead to be imaged by a solid state camera.

To view the lead without degrading the performance of the chamber, a viewing hole placed away from the area being examined and setting the optics so that the desired lead area is imaged. A cylindrical shaped light source 13 is mounted on the chamber to provide the uniform lighting inside the chamber.

The optical system is a stereo microscope 15 with a 7–20× magnification range and optics certified to meet resolution requirements for military inspection criteria. The microscope has a trinocular body to allow use of a solid state video camera 16. The microscope can also allow direct visual observation of the components if required.

The main controller of the inspection system is for example, an 80286, PC compatible computer with 8 bit and six 16 bit slots. Other computer systems may be used.

One example of a machine vision system consists of a set of boards that plug directly into the PC buss and is able to use all the peripherals of the PC. The vision system is not limited to the example given herein. A vision board 17a includes an image buffer that has four 512×512 pixel frame buffers and a complete library of standard vision analysis functions. The computer uses one parallel port for a standard dot matrix printer and the other port for a video image printer 21. The high resolution video image screen printer 21 prints pictures of the component lead being inspected, or images that have been stored on disk. A mouse 18 is connected through one of the serial ports as the user interface device.

System camera 16 has a pixel resolution depended upon the material being inspected. High or low resolution cameras may be used depending upon the application, and the capability to accurately resolve the gray levels on the lead surface. A black and white, solid state camera with 780×540 pixel image resolution and low level light sensitivity is used in one configuration. The user control panel for the system consists of a standard three button digital mouse 18 and a high resolution color monitor 19 for displaying easy to follow menu screens. The video monitor allows switching between the standard PC video output and the machine vision video output. Video monitor 19 can also provide a display of the image being printed by the video image printer. A special, multi-axes stepper controller card 17b is used by the PC to control the component positioning system. Stepper motor controller 17b is capable of controlling four axis of motion. The system utilizes both a linear 30 and rotational stepper 32 motor for parts placement in the light chamber and for rotating the component during inspection. A stepper driver 31 interfaces the linear stepper motor 30 with motor controller 17b, and another stepper driver 33 interfaces motor controller 17b with the rotary motor.

A tool 36 for holding a component is, for example, a static controlled, component gripping tool with two degrees of freedom (linear and rotational). Positioning of the gripper is controlled through the computer by the linear and rotational stepper motors 30,32. The gripper is capable of holding axial components with body diameters ranging in size from 0.06 to 0.5 inches. The gripper holds the component by the body. A slip clutch is used to prevent damage to the component body when the gripper is closed. During operation, tool 36 positions each component so the entire circumference of a one inch long lead can be inspected. The ends of the grippers are designed to prevent interference with the lighting of the component and to allow the vision system to locate the end of the component body.

Figure 3:
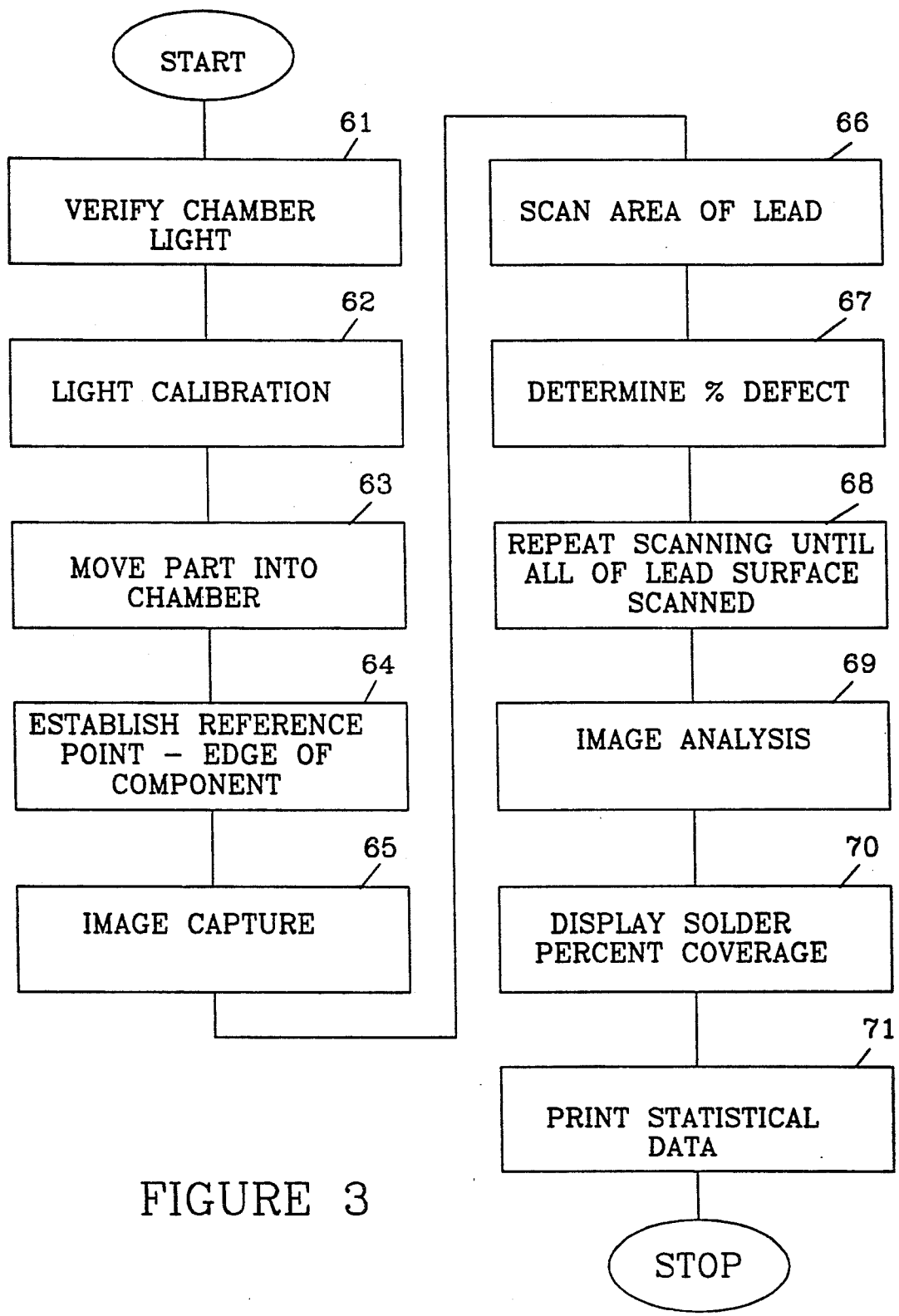
FIG. 3 is a flow diagram of the method of the present invention.

FIG. 3 is a process flow diagram of the method of the present invention. The first step in inspecting a component lead is loading the part. Once the desired part is loaded, an execute command is selected on a menu screen and the system verifies the inspection chamber lighting 61. If not correct, the system displays a setup screen that allows the operator to interactively set the correct lighting level 62. The system then moves the part into the illumination chamber 63. As the part enters the field of view of the camera, the vision system establishes a reference point 64 on the edge of the component body and performs a calibration procedure. This calibration procedure ensures that the system begins inspecting the lead 50 mils from the component body, which is one of the MIL-STD-202 requirements. The computer then begins inspecting the component lead 65. The part positioning system moves an area of the lead under the microscope for inspection 66. The vision system analyzes the viewed portion of the lead and determines the percent defect area 67. This process is repeated 68 until the entire lead is inspected. Upon completion of the inspection operation, the system displays the total solder coverage on the monitor 70, prints 71 desired statistical data on a dot matrix printer (i.e. largest defect found, defect density, per field of view solder coverage, etc...), and returns the part to home position so the next part can be loaded.

In the image capture step 65, the image system views the lead. The defects or voids in the solder coating on the leads appear darker than the solder coating. Using this effect, the system counts the number of pixels within a predefined range of gray scale. By comparing the number of dark pixels counted against the total pixel area of the component lead, the percent of solder coverage can be calculated.

Color mapping may be used to enhance the display of defects. Color mapping assigns the gray scale values a color. Since the human eye can distinguish colors better than gray scales, the defects are easier to identify when displayed on a color monitor.

What is claimed is:

1. A method for determining the quality of solder coating on leads of electronic components inserted into a viewing chamber, comprising the steps of:
   illuminating the lead, inside he viewing chamber, to be inspected;
   verifying the intensity of the light in the viewing chamber
   calibrating the light in the viewing chamber;
   establishing a reference point at the edge of the component adjacent the lead;
   viewing the lead with a vision system;
   determining if there is a solder coating on the component lead;
   mapping and resolving, with the vision system, the surface of the lead into a plural of pixels, while rotating the component and lead;
   comparing the light, on a pixel-by-pixel basis, reflected from the surface of the lead;
   determining the number of pixels representing reflected light that fall below a predetermined intensity level representing defect areas in the coating;
   comparing the number of pixels that fall below a predetermine intensity with the total number of pixels for the lead to determine the percent of defect area of the lead surface.

2. The method according to claim 1, wherein mapping of the lead surface begins approximately 50 mils from a component body.

3. The method according to claim 1, wherein the reflected light intensity for each pixel is coded into a gray scale value.

4. The method according to claim 3, wherein the gray scale value is assigned a color for display surfaces.

5. A method for determining the quality of solder coating on leads of electronic components using light reflected from the surface of the lead, comprising the steps of:
   calibrating the light used for illumining the lead prior to mapping of the lead surface;
   mapping and resolving, with a vision system, the surface of a lead into a plurality of pixels; and
   rotating the lead during mapping to map the entire surface of the lead;
   determining the number of pixels, compared with the total number of pixels that represent a surface of the lead, that represent reflected light, reflected from the component surface, that has an intensity below a predetermined intensity level.

6. The method according to claim 5, including the step of locating the end of a component body adjacent the lead to establish a reference point prior to mapping the lead surface.

7. The method according to claim 5, wherein mapping of the lead surface begins approximately 50 mils from the component body.

8. The method according to claim 5, wherein the reflected light intensity for each pixel is coded into a gray scale value.

9. The method according to claim 8, wherein the gray scale value is assigned a color for display purposes.

10. The method according to claim 5, including the step of determining if the component being inspected has a solder coating on the lead.

11. A method for detecting defects in a surface of an object, comprising the steps of:
   mapping and resolving, while rotating the object, with a vision system, the surface of the object into a plurality of pixels; and
   determining the number of pixels, compared with the total number of pixels that represent a surface of the object, that represent reflected light, reflected from the object surface, that has an intensity below a predetermined intensity level.

* * * * *